|   | United States Patent [19] | [11] | 4,260,833 |
|---|---|---|---|
|   | Firth | [45] | Apr. 7, 1981 |

[54] PREPARATION OF ALKYLPHENOLS

[75] Inventor: Bruce E. Firth, Arlington Heights, Ill.

[73] Assignee: UOP Inc., Des Plaines, Ill.

[21] Appl. No.: 99,222

[22] Filed: Nov. 30, 1979

[51] Int. Cl.³ .................. C07C 37/11; C07C 37/14
[52] U.S. Cl. ..................... 568/789; 568/794
[58] Field of Search .................... 568/789, 794, 784

[56] References Cited
U.S. PATENT DOCUMENTS

| 3,290,389 | 12/1966 | Hahn ................................. 568/781 |
| 3,367,981 | 2/1966 | Napolitanoe ....................... 568/789 |
| 3,670,030 | 6/1972 | Sparks ................................. 568/789 |

*Primary Examiner*—Werren B. Lone
*Attorney, Agent, or Firm*—James R. Hoatson, Jr.; Raymond H. Nelson; William H. Page, II

[57] ABSTRACT

A process for introducing a plurality of alkyl groups into the aromatic ring of a hydroxy-substituted aromatic compound comprises contacting said aromatic compound with an olefin in the presence of a lithiated alumina as catalyst and recovering the product. When said aromatic compound is phenol, said olefin is iso-butylene, and said catalyst is lithiated alumina, 2,4-di-t-butylphenol is formed with superior selectivity.

2 Claims, No Drawings

PREPARATION OF ALKYLPHENOLS

BACKGROUND OF THE INVENTION

It has been known for some time that certain hydroxy aromatic compounds are effective antioxidants useful in a wide range of applications. For example, the food additive commonly known as BHA is 2-t-butyl-4-methoxyphenol. Other phenols have been utilized as antioxidants in petroleum products, in plastics, in lubricants, and in other applications where increased oxidative stability is desired. Certain polyalkylated hydroxy-substituted aromatics are especially effective antioxidants. Thus, 2,4-di-t-butylphenol is of commercial utility as an antioxidant when added to fuel oils. To utilize the antioxidant properties of such compounds it is incumbent to have a method of selectively alkylating hydroxy-substituted aromatic compounds in the position ortho to the hydroxy group.

The methods of alkylating hydroxy-substituted aromatic compounds are legion and well known to the skilled artisan in this field. Those methods based on strong acids, such as phosphoric and sulfuric acids, or strong Lewis acids, such as aluminum chloride, possess the disadvantage that considerable intramolecular rearrangement, disproportionation, and transalkylation attend the desired alkylation. Thus, the final product using such catalysts tends to reflect thermodynamic control, i.e., given sufficient time an equilibrium mixture will result. For example, monoalkylation of P-cresol with introduction of the group R using the above catalysts may give a mixture of products according to the reaction,

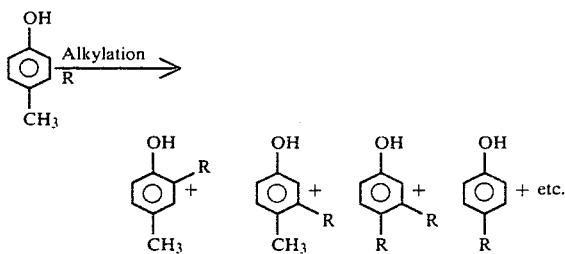

Since an object of the present invention is to provide compounds having at least one alkyl group ortho to the hydroxyl, and since such compounds generally are not thermodynamically more favored than other isomeric alkylated hydroxy-substituted aromatic compounds, the kinds of catalysts described above are unsuitable for efficient synthesis of these products. An additional disadvantage of these catalysts is that the reaction product is a complex mixture of isomers and homologs so that separation of pure components is a difficult if not a near-impossible task.

Use of weaker Lewis acids as catalysts alleviates the problem somewhat. Thus, in U.S. Pat. Nos. 3,290,389 and 3,367,981 are described processes in which alumina is used to alkylate phenols with preferential introduction of alkyl groups of the ortho position. However, because alumina is a relatively weak acid its catalytic activity is low relative to the stronger acids discussed above, necessitating minimum reaction temperatures of about 250° C. and above for several hours to achieve polyalkylation. At these reaction conditions several undesirable side reactions may occur, such as oligomerization of the olefin used as the alkylating agent, thermal cracking to some of the reaction products, and significant disproportionation of some of the alkylated phenols thus formed, i.e., dealkylation. All these reactions are undesirable in the context of affording products containing relatively less of those phenols having the greatest antioxidant properties, in the context of affording complex mixtures from which separation of the most desirable component is difficult and tedious, and in the context that one of the reactants is consumed to give useless by-products.

SUMMARY OF THE INVENTION

A principal object of this invention is to provide a process of introducing a plurality of alkyl groups into the aromatic ring of a hydroxy-substituted aromatic compound with an olefin in the presence of doped alumina. An embodiment of this invention comprises the use of this process wherein the alumina contains from about 0.1% to about 2% lithium ion. A more specific embodiment comprises the process wherein the alumina contains from about 0.1% to about 2% lithium and the olefin is isobutylene.

Other objects and embodiments will be apparent from the description herein.

DESCRIPTION OF THE INVENTION

The alkylation of phenols by olefins in the presence of a catalyst is a reaction of substantial importance. Its use in the preparation of polyalkylated hydroxy-substituted aromatic compounds where the unsubstituted positions of the aromatic ring ortho to the hydroxyl group are preferentially alkylated poses a challenge. On the one hand, use of highly active catalysts tends to lead to thermodynamically controlled mixtures, where the ortho alkylated product is merely one of many components. On the other hand, use of less active catalysts leads to low conversions of the reactants and permits incursion of unwanted side reactions. Another important factor is the recognition that alkylation at the ortho position is sterically hindered. Such steric hindrance is especially important where a tertiary alkyl group is sought to be introduced, for ortho alkylation may be disfavored kinetically as well as thermodynamically.

Alumina, especially in its gamma form, is an attractive compromise as a catalyst for introduction of tertiary alkyl groups. However, the use of alumina to achieve polyalkylation of aromatic compounds with olefins generally requires a temperature in excess of 250° C., and at these temperatures oligomers of the olefin may be formed in substantial amounts.

Doped alumina is an alumina which has been treated with an inorganic material such that inorganic ions have been deposited therein. Lithiated alumina is an example of a doped alumina, and is an alumina which contains lithium ions, lithiated alumina being less acidic than alumina itself. When used in the present specification and appended claims, "doped alumina" will mean lithiated alumina.

A discovery of this invention is that use of lithiated alumina, depsite its lower acidity, affords a more selective alkylation of phenols than alumina itself at temperatures less than about 250° C., and without oligomerization at extended reaction times. Lithiated alumina is a product wherein lithium ions have been deposited in the alumina matix. It may be prepared, for example, by contacting alumina with a solution of a suitable lithium salt, such as lithium nitrate, evaporating the water while mixing, and calcining the resultant product. Preparations containing from about 0.1 to about 2 weight percent lithium are preferred, and those from about 0.1 to about 1 weight percent lithium are particularly preferred. Reaction temperatures which are employed in the alkylation of a hydroxy-substituted aromatic compound may be from about 150° C. to about 350° C. and even higher, but the maximum reaction temperature is preferably about 250° C. Operation at pressures from 1 atmosphere to those in excess of 250 atmospheres is possible, with the reaction time being from about 1 to about 30 hours.

Another advantage of the use of lithiated alumina in this invention is that oligomerization of the olefinic component of the reaction, especially terminally disubstituted olefins, is minimal or, frequently, does not occur at all under reaction conditions. Still another advantage of lithiated alumina is that it does not effect dealkylation, as does alumina. Thus, for example, if 2,4-di-t-butylphenol is heated in the presence of alumina there is formed 4-t-butylphenol by preferential dealkylation of the ortho t-butyl group.

The inability of lithiated alumina to effect dealkylation under reaction conditions is especially desirable when the various products of reaction are not to be separated, and when there is a preference for one minor component over another. For example, in some processes affording 2,4-di-t-butylphenol as the major component, the chief minor component is a monalkylated product, resulting in part from dealkylation. If the mixture is to be used as an antioxidant, there is a substantial advantage when the monalkylated phenol is chiefly 2-t-butylphenol rather than the 4-isomer. The use of lithiated alumina favors formation of the 2-monoalkylphenol, and thus possesses a substantial advantage vis-a-vis other catalysts which fail to achieve this result.

The process of this invention may be applied to a broad variety of hydroxy-substituted aromatic compounds wherein the aromatic ring may contain one or more other substituents, as aryl, alkyl, aralkyl, alkaryl, hydroxy, alkoxy, aryloxy, alkanoyloxy, amino, alkylamino, arylamino, dialkylamino, diarylamino, mercapto, alkylmercapto, and arylmercapto moieties. The process of this invention may also be applied to said aromatic compounds wherein the aromatic system is a fused-ring aromatic compound, such as naphthalene, anthracene, and the like, which may also bear one or more other substituents such as those enumerated above. Examples of suitable hydroxy-substituted aromatic compounds include the cresols, ethylphenol, butylphenol, hydroquinone, hydroxyanisole, hydroxyaniline, naphthol, methylhydroxybenzoate, methylmercaptophenol, ethylmercaptophenol, phenylmercaptophenol, hydroxydiphenylether, dimethylaminophenol, dibutylaminophenol, and benzylphenol.

Olefins that may be used are of the structural type $R_1R_3C=CHR_2$, where $R_1$, $R_2$, and $R_3$ are selected from the group consisting of hydrogren, and alkyl moiety having from 1 to about 20 carbon atoms, an aryl group such as phenyl, naphthyl, and substituted aryl groups. Specific examples of olefins which may be employed include ethylene, propylene, butylene, the isomeric amylenes, isomeric hexylenes, isomeric heptylenes, isomeric octalenes, the linear internal olefins resulting from commercial dehydrogenation of n-alkanes in the $C_{10}$-$C_{18}$ range, and the isomeric eicosenes. Olefins in which neither $R_1$ nor $R_3$ is hydrogen are particularly preferred, i.e., terminally disubstituted olefins, which afford tertiary alkyl groups upon introduction into the aromatic ring. Examples of such olefins, cited solely for illustrative purposes and not by way of limitation, include isobutylene, 2-methyl-1-butene, 2-methyl-2-butene, 2-ethyl-1-pentene, 2,3,dimethyl-1-butene, 3-methyl-2-pentene, 2-methyl-1-pentene, 2-methyl-2-pentene, etc.

Isobutylene is an especially desirable example for the latter group of olefins used in this invention. Among the compounds which may be made by this process are di-t-butylphenol, tri-t-butylphenol, di-and tri-t-butylphenol, di-and tri-t-amylphenol, di-and tri-t-hexylphenol, di-and tri-t-decylphenol, di-and tri-t-eicosylphenol, 2-t-butyl-4-methylphenol, 2-t-hexyl-4-methylphenol, etc.

The process of this invention may be utilized in the batch mode. For example, a suitable reactor, such as that of the rocking autoclave type, is charged with the desired amount of hydroxy-substituted aromatic compound and lithiated alumina. Thereupon, the olefin is added, and if it is desired to conduct the reaction at a pressure other than that indigenous to the various components, a suitable inert gas is admitted to the desired pressure. The reactor is sealed, mixing is commenced, and the contents are heated to the predetermined temperature. This reaction temperature is maintained for the time necessary for optimum yield of the alkylated product, generally from about 1 to about 20 hours. After the mixture is cooled, the apparatus is vented, the catalyst is removed by suitable means, for example, by filtration, and product is recovered.

The process of this invention also may be practiced in a continuous mode. A reactor may contain a bed of lithiated alumina heated and maintained at the desired temperature. A mixture of hydroxy-substituted aromatic compound and olefin may be passed through the bed at a rate such that the total contact time of reactants optimizes the product composition. Olefin and unconverted reactant may be separated from the effluent and recirculated. Product may be recovered from the effluent by suitable means, for example, by distillation.

The following examples illustrate the process described in this invention. It is to be understood that said enumerated olefins and hydroxy-substituted aromatic compounds are merely representative of the class of compounds which may be used and the present invention is not necessarily limited thereto.

All reactions were run in a 300-ml. rocking autoclave. The general procedure was to charge the autoclave with the desired amount of the hydroxy-substituted aromatic compound and the catalyst, following which the olefin used for alkylation was introduced. The reaction mixture was heated to the specified temperature and maintained there for the specified time. When the olefin used was isobutylene, initial pressures ranged up to about 100 atmospheres. At the end of the reaction, the mixture was allowed to cool and, in the case of gaseous olefins, excess olefin was vented. The catalyst was separated by decantation and filtration, and the composition of the mixture was determined by gas-liquid partition chromatography (glpc).

EXAMPLE 1

A mixture of phenol (25 g, 0.27 mole), isobutylene (1.6 mole, 6-fold excess), and 20 g of alumina was reacted at 250° C. for 4 hours. Examination of the product by glpc showed it consisted of only 37% of 2,4-di-t-butylphenol, the remainder being 2-t-butylphenol (49%), 4-t-butylphenol (4%), 2,6-di-t-butylphenol (4%), 2,4,6-tri-t-butylphenol (2%), and phenol (4%).

EXAMPLE 2

A mixture of phenol (25 g, 0.27 mole), isobutylene (1.6 mole, 6-fold excess), and 20 g of 0.3% lithiated alumina was reacted at 250° C. for 8 hours. The product consisted of 2,4-di-t-butylphenol (79%), 2-t-butylphenol (10%), 4-t-butylphenol (5%), and 2,4,6-tri-t-butylphenol (5%). Oligomers were not formed to any appreciable extent.

Comparison of these results show that at the same temperature lithiated alumina shows substantially improved selectivity and yield in formation of the desired 2,4-di-t-butylphenol without undesirable oligomerization or dealkylation, despite doubled reaction time.

What is claimed is:

1. A process for producing 2,4-di-t-butylphenol which comprises reacting phenol and isobutylene at a temperature from about 150° C. to about 350° C., at a pressure from about 1 to about 250 atmospheres, and for a time period from about 1 to about 20 hours in contact with lithiated alumina to produce said 2,4-di-t-butylphenol as the major product of the process, and recovering the resultant product.

2. The process of claim 1 wherein said lithiated alumina contains from about 0.1 to about 2 weight percent of lithium.

* * * * *